United States Patent [19]

Ellis et al.

[11] Patent Number: 4,710,476
[45] Date of Patent: Dec. 1, 1987

[54] SURFACE-DERIVATIZED SEMICONDUCTORS WITH CHEMICALLY SENSITIVE LUMINESCENCE

[75] Inventors: Arthur B. Ellis; Hal van Ryswyk, both of Madison, Wis.

[73] Assignee: Minnesota Mining and Manufacturing Company, St. Paul, Minn.

[21] Appl. No.: 811,511

[22] Filed: Dec. 20, 1985

[51] Int. Cl.$^4$ ............................................. G01N 21/63
[52] U.S. Cl. ....................................... 436/172; 422/88; 422/91
[58] Field of Search ..................... 356/445; 422/86, 88, 422/91, 98; 436/84, 164, 167, 172

[56] References Cited

PUBLICATIONS

McQuarrie et al; General Chemistry; W. H. Freeman and Co., New York, 1984, pp. 781–803.
Carpender et al; Photoluminescent Response of Pd–CdS and Pd–CdS$_x$Se$_{1-x}$ Schottky Diodes to Molecular Hydrogen; Langmuir 1985 1, 605–607.
"Preparation of Chemically Derivatized Platinum etc",
M. S. Wrighton et al., J.A.C.S., 100:23, Nov. 8, 1978, pp. 7264–7270.
"The Reduction of Iodine at GaAs: etc.", J.E.A.M. van der Meerakker, J. Electrochem. Soc. 30, 1985, pp. 435–440.
"Chemically Derivatized n-Type Semiconducting Gallium Arsenide Photoelectrodes etc.", J. M. Bolts et al., J.A.C.S., 100, 1979, pp. 6179–6183.
"Covalently Attached Organic Monolayers on Semiconductor Surfaces", Ivan Haller, J.A.C.S., 100, 1978, pp. 8050–8055.

Primary Examiner—Barry S. Richman
Assistant Examiner—Michael S. Gzybowski
Attorney, Agent, or Firm—Donald M. Sell; James A. Smith; Mark A. Litman

[57] ABSTRACT

The presence of certain chemicals on the emitting surface of the surface-derivatized photoluminescent semiconductor alters the characteristics of radiation emitted from said surface. This alteration is used to indicate the presence of those chemicals in the environment.

12 Claims, 1 Drawing Figure

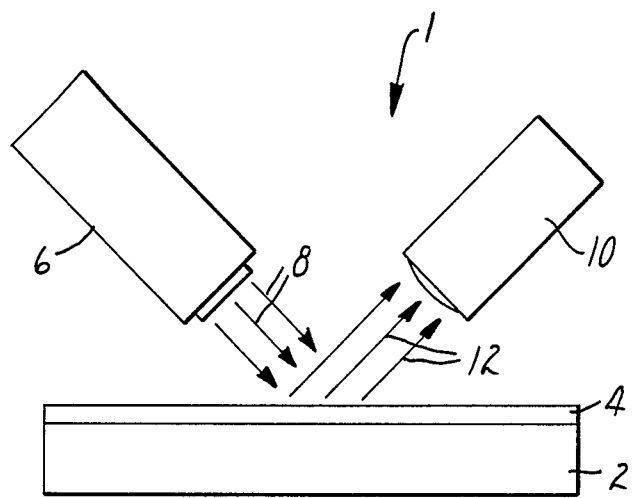

SURFACE-DERIVATIZED SEMICONDUCTORS WITH CHEMICALLY SENSITIVE LUMINESCENCE

TECHNICAL FIELD

The present invention relates to optically coupled chemical sensing devices and to processes for detecting the presence of certain classes of chemical compounds.

BACKGROUND OF THE ART

Electroluminescence occurs in semiconductor materials which are capable of emitting visible or near visible radiation when an electrical current passes through the semiconductor. Photoluminescence can also occur in these materials. If external light is used to excite the semiconductor, a characteristic wavelength of light is emitted. These characteristic wavelengths vary amongst different photoluminescent semiconductors and can be varied in a single semiconductor by doping or changing the composition of the material.

Amongst the various studies on the luminescence of photostimulated or electroluminescent materials is "Luminescent Photoelectrochemical Cells", Streckert, H. H., Tong, J. and Ellis, A. B., J. Am. Chem. Soc., Vol. 104, No. 2, 1982, pp. 581–588. It is noted therein that the intensity of light emitted by electroluminescence and photoluminescence varies directly with the applied voltage. The efficiency of charge transfer and good electrical contact at the surface is also noted as important in the efficiency of the process.

U.S. patent application Ser. No. 480,471 filed on Mar. 30, 1983 discloses semiconductor electrodes having multicolor luminescence. These semiconductors comprise solid state solutions of three elements which vary in a vertically anisotropic manner. The preferred solid state solutions are of cadmium, sulfur and selenium.

U.S. Pat. No. 4,211,586 discloses a method of forming a multicolor light-emitting array of diodes. The diodes are formed by differentially etching a graded n-type semiconductor and diffusing a p-type dopant into the surface of the n-type semiconductor to form a p-n junction diode.

U.S. patent application Ser. No. 712,799, filed Mar. 18, 1985, discloses an apparatus for detecting the presence of certain chemical compounds comprising a photoluminescent semiconductor having a metal coating on a radiation emitting surface of the semiconductor, a source of actinic radiation which can impinge on the radiation emitting surface of the semiconductor, and a means for detecting changes in the characteristics of radiation emitted from said radiation emitting surface. The absorption of hydrogen into the metal layer is suggested as varying the height of the Schottky barrier of the diode and causing a change in spectral characteristics of the radiation emitted.

SUMMARY OF THE INVENTION

The present invention describes an optically coupled sensing apparatus of a photoluminescent semiconductor, a source of actinic radiation which can impinge on a radiation emitting surface of the semiconductor and a means for detecting changes in the characteristics of the radiation emitted from the radiation emitting surface. The radiation emitting surface has reacted thereon a compound capable of undergoing oxidation and/or reduction, the redox product of which reacted compound has a vertical charge distribution therein with respect to the radiation emitting surface.

BRIEF DESCRIPTION OF THE DRAWING

The FIGURE shows a schematic representation of the sensing apparatus of the present invention.

DETAILED DESCRIPTION OF THE DRAWING

The FIGURE shows a schematic representation of the sensing device (1) of the present invention. The photoluminescent semiconductor layer (2) has a layer (4) of a compound capable of undergoing further oxidation or reduction reacted onto the surface of the semiconductor layer (2). A source (6) of actinic radiation (8) is provided to direct radiation (8) at the semiconductor layer (2). A detector (10) is provided to detect changes in the radiation (12) emitted from the semiconductor layer (2).

DETAILED DESCRIPTION OF THE INVENTION

The present invention uses the creation of electrical or ionic charges in compounds on the surface of photoluminescent semiconductors to alter or modulate the electric field of the semiconductor. The modulation of the electric field alters the photoluminescence of the semiconductor, and this alteration can be detected by sensing means.

A compound can be coated or preferably reacted onto the surface of the semiconductor. The coated material or reacted compound must be capable of a further redox reaction. Furthermore, the product of the redox reaction must be a moiety or moieties with a charge thereon or a separation of charges with a vertical displacement relative to the emitting surface of the photoluminescent semiconductor. The created charge distribution must have some vertical displacement therein or there will be no variation in the electric field. For example, if the redox reaction produced a change in positive or negative ionic centers on the redox reaction product which were equidistant from the semiconductor surface, there would be no alteration in the electric field.

Photoluminescent semiconductors are well known in the art. They are generally solid state solutions of at least two or three elements which, when stimulated by actinic radiation, emit radiation. Both the actinic and emitted radiation are generally visible or near visible radiation (300–900 nm). When a coating over the radiation emitting surface of the semiconductor is a material (such as ferrocene derivatives) which when oxidized or reduced alters the electric field in the semiconductor surface, the luminescence of the semiconductor has been found to be altered. Variations in photoluminescence are an indication of the presence of such oxidizing and reducing compounds.

Particularly useful n-type semiconductors which can be used to form the detectors according to the present invention are n-GaAs, n-GaAs$_x$P$_{1-x}$ (where x is from 0 to 1), CdS, CdSe, and CdS$_x$Se$_{1-x}$ ($0 \leq x \leq 1$) wherein the semiconductor may have a graded composition or not. Other useful semiconductors would be ZnSe:Al, Cd$_x$Zn$_{1-x}$S ($0 \leq x \leq 1$), ZnS$_x$Se$_{1-x}$ ($0 \leq x \leq 1$), Cd$_x$Zn$_{1-x}$Se ($0 \leq x \leq 1$), and the like. The redox reactive compound can be deposited on the elements according to standard manufacturing techniques and techniques shown by Wrighton, J. Am. Chem. Soc., 1979, 101, p. 6179.

A functional apparatus for actually using this phenomenon for detecting the presence of volatile oxidants and reductants would have at least the following 3 components: the coated semiconductor, a source of actinic radiation directed at the radiation emitting surface of the structure or sensor formed by the coating on the semiconductor, and an optical detector. The sensor or structure has already been described. The actinic radiation source may be merely an opening exposing the sensor or structure to available light (room light, sunlight, etc.) or may be any internal source of radiation such as a light bulb, light emitting diode, or laser. The radiometer may be selected from amongst the many commercially available radiometers, its selection being primarily dependent upon the ultimate sensitivity desired in the final article. Fiber optics may be used to carry actinic radiation to the diode or to carry emitted radiation away from the diode.

EXAMPLE 1

Samples of n-GaAs were prepared for derivatization by etching in 4:1:1 $H_2SO_4:H_2O_2$ (30% aqueous):$H_2O$ at 50° C. for 30 seconds, rinsed in water, immersed in 7M KOH at 50° C. for 30 minutes, rinsed again, and air-dried prior to derivatization. The samples prior to preparation were noted as n-GaAs:Te with carrier concentrations of $8 \times 10^{16}$ cm$^{-3}$ and <100> orientation. A ferrocene derivative, (1,1'-ferrocenediyl)dichlorosilane was reacted with the n-GaAs substrate in isooctane solution according to the teachings of Wrighton, J. Am. Chem. Soc., 1979, 101, p. 6179.

When the sensor was illuminated with ultrabandgap light, the bandgap photoluminescence (PL) of the GaAs substrate (865 nm in the near IR) was sensitive to gaseous oxidants. For example, gaseous $I_2$ or $Br_2$ caused the PL intensity to quench approximately 50%. This effect appeared to be irreversible in air, although strong volatile reducing agents such as hydrazine reversed the effect. The system was also regenerated by using the sample as an electrode in acetonitrile (n—$Et_4N^+BF_4^-$ supporting electrolyte) and applying a cathodic pulse to reduce the Fe to its original oxidation state. Cyclic voltammetry in this electrolyte indicated that the surface coating was present in at most several monolayers of coverage. The sensor was unaffected by gases such as air, CO, $CH_4$, and $H_2$ in both the oxidized and reduced states. Although somewhat resistant to water vapor, high concentrations of water vapor in combination with strong oxidizing agents such as $Br_2$ or chlorine brought about the destruction of the sensor's surface.

EXAMPLES 2-4

Example 1 was repeated except that the photoluminescent semiconductors used in the substrate were CdS, $GaAs_{0.7}P_{0.3}$ and $CdS_{0.9}Se_{0.1}$. The apparatus was found to detect the presence of $Br_2$ and $NO_2$.

We claim:

1. An apparatus for detecting the presence of chemical compounds comprising:
   (1) a photoluminescent semiconductor having on a radiation emitting surface thereof a reacted material bonded to said radiation emitting surface of said semiconductor, said reacted material being capable of undergoing a redox reaction with an oxidizing or reducing compound to produce a redox product bonded to said radiation emitting surface, which reacted material has an ionic charge distribution which is vertical with respect to the radiation emitting surface, said charge distribution being capable of altering an electric field in said semiconductor,
   (2) a source of actinic radiation which impinges on said radiation emitting surface of said semiconductor, and
   (3) a means for detecting changes in the radiation emitted from said radiation emitting surface.

2. The apparatus of claim 1 wherein said source of radiation comprises visible light.

3. The apparatus of claim 1 wherein said semiconductor comprises a solid state solution of at least two elements selected from the group consisting of (a) cadmium, selenium and sulfur, (b) zinc, selenium and sulfur, (c) cadmium, zinc and selenium, (d) cadmium, zinc and sulfur, (e) cadmium and selenium, (f) cadmium and sulfur, (g) zinc and selenium doped with aluminum, (h) gallium and arsenic, (i) gallium, arsenic and phosphorus, and (j) gallium and phosphorus.

4. The apparatus of claim 3 wherein said means for detecting changes in the characteristics of the radiation is a radiometer.

5. The apparatus of claim 3 wherein said reacted material comprises a ferrocene compound.

6. The apparatus of claim 1 wherein said means for detecting changes in the characteristics of the radiation is a radiometer.

7. The apparatus of claim 6 wherein said source of radiation comprises visible light.

8. The apparatus of claim 6 wherein said reacted material comprises a ferrocene compound.

9. The apparatus of claim 8 wherein said source of radiation comprises visible light.

10. The process for detecting the presence of chemical components comprising providing a photoluminescent semiconductor having on at least one radiation emitting surface a reacted material bonded to said radiation emitting surface, said reacted material being capable of undergoing a redox reaction with an oxidizing or reducing compound to produce a redox product bonded to said radiation emitting surface, which reacted material has an ionic charge distribution which is vertical with respect to the radiation emitting surface, said charge distribution being capable of altering an electric field in said semiconductor, irradiating said surface with actinic radiation, observing the radiation emitted from said surface, then exposing said surface to an environment having chemical compounds capable of oxidizing or reducing said reacted material therein and detecting any changes in the radiation emitted from said surface.

11. The process of claim 10 wherein said actinic radiation is visible light.

12. The process of claim 10 wherein light from a light bulb, laser, or light emitting diode provides said actinic radiation.

* * * * *

UNITED STATES PATENT AND TRADEMARK OFFICE
CERTIFICATE OF CORRECTION

PATENT NO. : 4,710,476

DATED : December 1, 1987

INVENTOR(S) : Arthur B. Ellis, et. al.

It is certified that error appears in the above-indentified patent and that said Letters Patent is hereby corrected as shown below:

Column 1, line 4, insert under Title: This invention was made with Government support under Contract N00014-85-k-0631 awarded by the Department of the Navy. The Government has certain rights in the invention.

Signed and Sealed this

Sixteenth Day of November, 1993

Attest:

BRUCE LEHMAN

Attesting Officer

Commissioner of Patents and Trademarks